US00PP33606P2

(12) United States Plant Patent
Flore

(10) Patent No.: US PP33,606 P2
(45) Date of Patent: Nov. 2, 2021

(54) ***PHALAENOPSIS* PLANT NAMED 'MI01526'**

(50) Latin Name: *Phalaenopsis hybrida*
Varietal Denomination: MI01526

(71) Applicant: Febe Flore, Lochristi (BE)

(72) Inventor: Febe Flore, Lochristi (BE)

(73) Assignee: Microflor N.V., Lochristi (BE)

( * ) Notice: Subject to any disclaimer, the term of this patent is extended or adjusted under 35 U.S.C. 154(b) by 0 days.

(21) Appl. No.: 17/163,520

(22) Filed: Jan. 31, 2021

(51) Int. Cl.
*A01H 5/02* (2018.01)
*A01H 6/62* (2018.01)

(52) U.S. Cl.
USPC ..... Plt./311
CPC ..... *A01H 6/62* (2018.05)

(58) Field of Classification Search
USPC ..... Plt./311
CPC ..... A01H 6/62
See application file for complete search history.

(56) References Cited

PUBLICATIONS

UPOV hit on *Phalaenopsis* plant named, 'MI01526', QZ PBR 2020/1126, filed Apr. 27, 2020.*

* cited by examiner

*Primary Examiner* — Anne Marie Grunberg
(74) *Attorney, Agent, or Firm* — C. Anne Whealy

(57) ABSTRACT

A new and distinct cultivar of *Phalaenopsis* plant named 'MI01526', characterized by its upright plant habit; vigorous growth habit; strong flowering stems; strong and relatively small leaves; freely flowering habit with typically two inflorescences per plant, each inflorescence with numerous flowers; light yellow green-colored flowers with red purple-colored centers and labella; and good postproduction longevity and resistance to bud drop during transport.

2 Drawing Sheets

Figure 1:
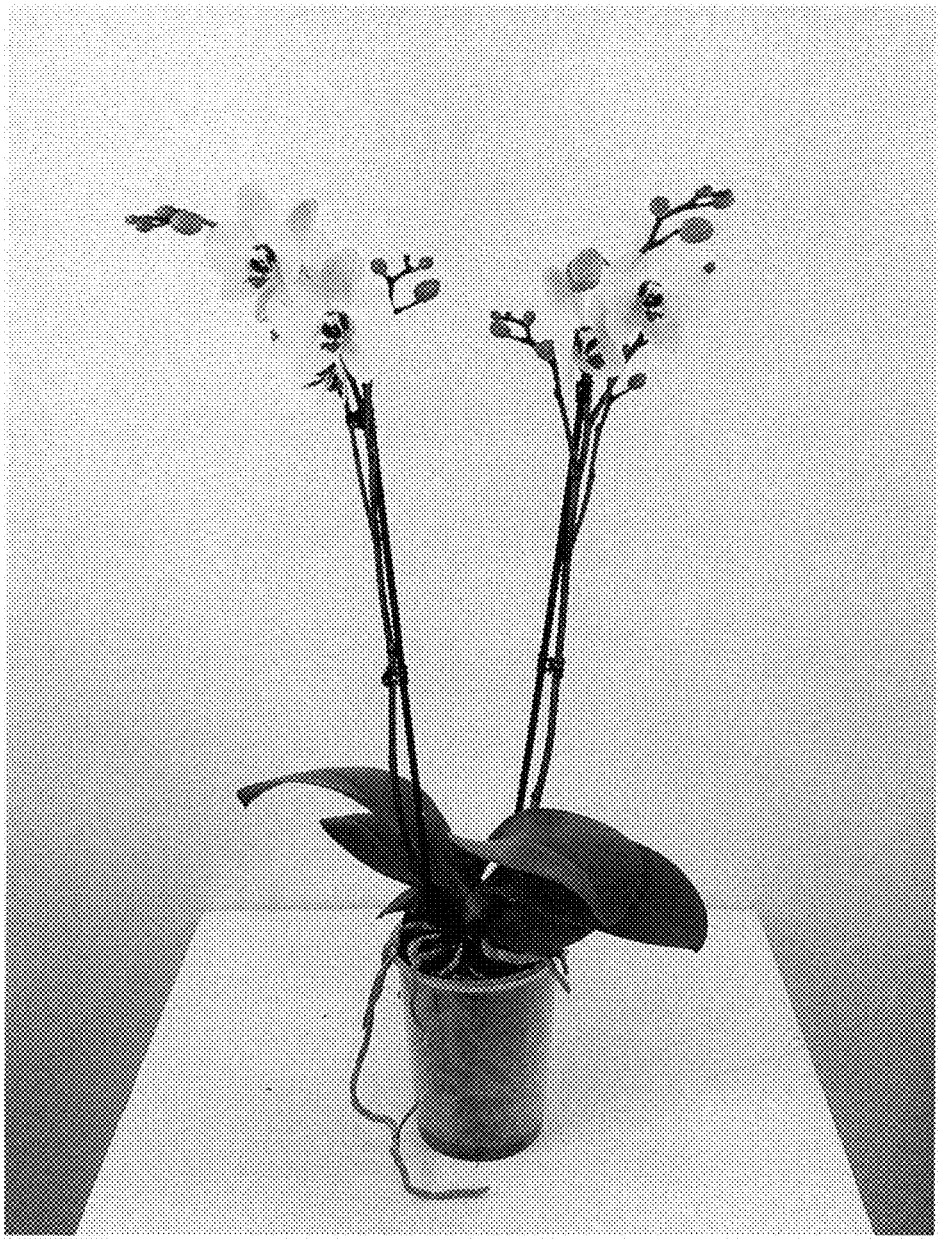

Botanical designation: *Phalaenopsis hybrida.*
Cultivar denomination: 'MI01526'.

STATEMENT REGARDING PRIOR DISCLOSURES BY INVENTOR/APPLICANT

An European Community Plant Breeder's Rights application for the instant plant was filed by the Assignee of the instant application, Microflor N.V. of Lochristi, Belgium on Apr. 27, 2020, application number 2020/1126. Foreign priority is not claimed to this application.

The Inventor/Applicant and Assignee assert that no publications nor advertisements relating to sales, offers for sale or public distribution occurred more than one year prior to the effective filing date of this application. Any information about the claimed plant would have been obtained from a direct or indirect disclosure from the Inventor/Applicant and/or the Assignee. Inventor/Applicant and Assignee claim a prior art exemption under 35 U.S.C. 102(b)(1) for disclosure and/or sales prior to the filing date but less than one year prior to the effective filing date.

BACKGROUND OF THE INVENTION

The present invention relates to a new and distinct cultivar of *Phalaenopsis* plant, botanically known as *Phalaenopsis hybrida*, and hereinafter referred to by the name 'MI01526'.

The new *Phalaenopsis* plant is a product of a planned breeding program conducted by the Inventor in Lochristi, Belgium. The objective of the breeding program is to develop new freely flowering *Phalaenopsis* plants with good leaf shape and flowers with unique and attractive flower coloration.

The new *Phalaenopsis* plant originated from a cross-pollination by the Inventor in July, 2013 in Lochristi, Belgium of a proprietary selection of *Phalaenopsis hybrida* identified as code number PHM00322, not patented, as the female, or seed, parent with a proprietary selection of *Phalaenopsis hybrida* identified as code number PHM00313, not patented, as the male, or pollen, parent. The new *Phalaenopsis* plant was discovered and selected by the Inventor as a single flowering plant from within the progeny of the stated cross-pollination grown in a controlled greenhouse environment in Lochristi, Belgium in February, 2016.

Asexual reproduction of the new *Phalaenopsis* plant by in vitro meristem propagation in a controlled environment in Lochristi, Belgium since June, 2017 has shown that the unique features of this new *Phalaenopsis* plant are stable and reproduced true to type in successive generations.

SUMMARY OF THE INVENTION

Plants of the new *Phalaenopsis* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'MI01526'. These characteristics in combination distinguish 'MI01526' as a new and distinct *Phalaenopsis* plant:

1. Upright plant habit.
2. Vigorous growth habit.
3. Strong flowering stems.
4. Strong and relatively small leaves.

5. Freely flowering habit with typically two inflorescences per plant, each inflorescence with numerous flowers.
6. Light yellow green-colored flowers with red purple-colored centers and labella.
7. Good postproduction longevity and resistance to bud drop during transport.

Plants of the new *Phalaenopsis* can be compared to plants of the female parent selection. Plants of the new *Phalaenopsis* differ primarily from plants of the female parent selection in the following characteristics:

1. Plants of the new *Phalaenopsis* are more vigorous than plants of the female parent selection.
2. Plants of the new *Phalaenopsis* have larger flowers than plants of the female parent selection.
3. Flowers of plants of the new *Phalaenopsis* are light yellow green in color with red purple-colored centers and labella whereas flowers of plants of the female parent selection are yellow in color with purple-colored spots.

Plants of the new *Phalaenopsis* can be compared to plants of the male parent selection. Plants of the new *Phalaenopsis* differ primarily from plants of the male parent selection in the following characteristics:

1. Plants of the new *Phalaenopsis* have slightly smaller flowers than plants of the male parent selection.
2. Flowers of plants of the new *Phalaenopsis* are light yellow green in color with red purple-colored centers and labella whereas flowers of plants of the male parent selection are white in color with yellow-colored centers and labella.

Plants of the new *Phalaenopsis* can be compared to plants of *Phalaenopsis hybrida* 'Rommé', not patented. In side-by-side comparisons, plants of the new *Phalaenopsis* differ primarily from plants of 'Rommé' in the following characteristics:

1. Plants of the new *Phalaenopsis* have smaller inflorescences than plants of 'Rommé'.
2. Plants of the new *Phalaenopsis* have inflorescences that are typically panicles and occasionally racemes whereas plants of 'Rommé' have inflorescences that are typically racemes.

BRIEF DESCRIPTION OF THE PHOTOGRAPHS

The accompanying photographs illustrate the overall appearance of the new *Phalaenopsis* plant showing the colors as true as it is reasonably possible to obtain in colored reproductions of this type. Colors in the photographs may differ slightly from the color values cited in the detailed botanical description which accurately describe the colors of the new *Phalaenopsis* plant.

The photograph on the first sheet (FIG. 1) is a side perspective view of a typical flowering plant of 'MI01526' grown in a container.

Figure 2:
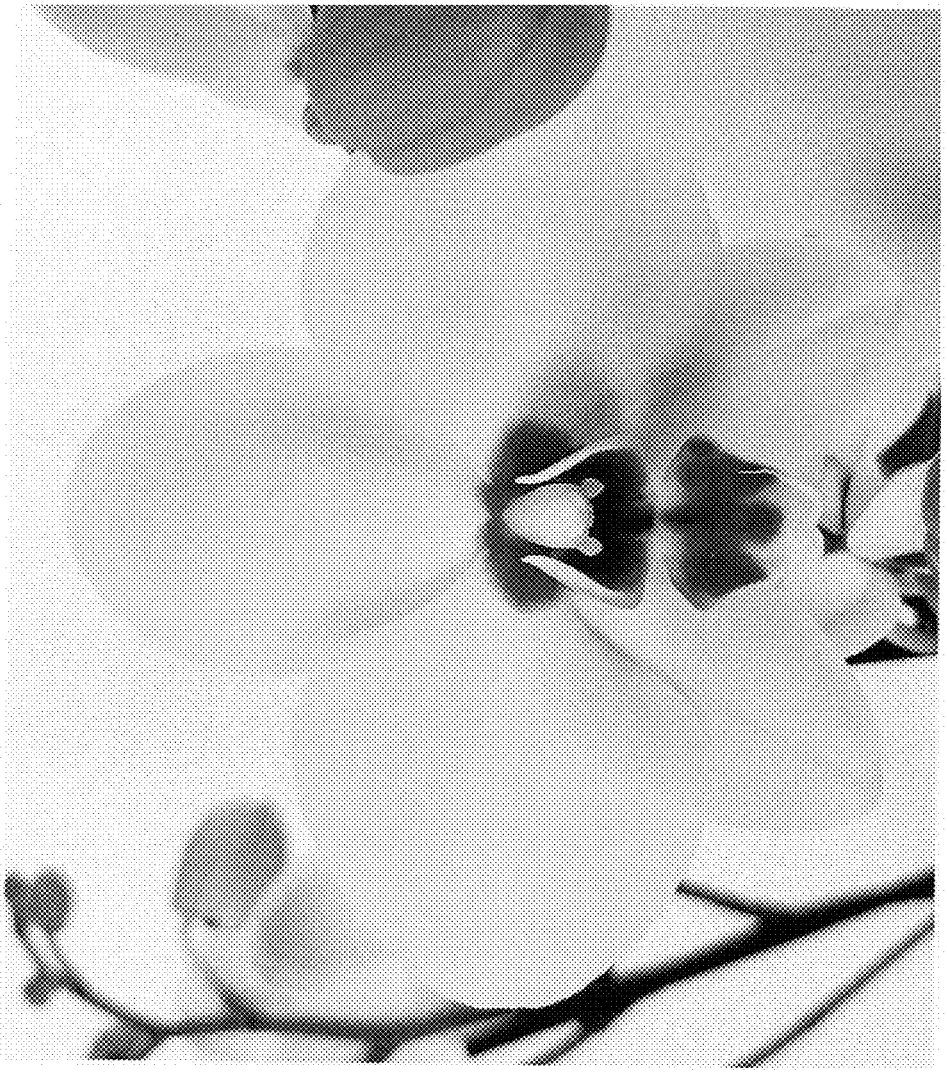

The photograph on the second sheet (FIG. 2) is a close-up view of a typical flower of 'MI01526'.

DETAILED BOTANICAL DESCRIPTION

The aforementioned photographs and following observations and measurements describe plants grown during the late summer in 12-cm containers in a glass-covered greenhouse in Lochristi, Belgium and under cultural practices typically used in commercial *Phalaenopsis* production. During the production of the plants, day and night temperatures ranged from 18° C. to 29° C. and light levels ranged from 150 Watt/m$^2$ to 375 Watt/m$^2$. Plants were 70 weeks old when the photographs and description were taken. In the following description, color references are made to The Royal Horticultural Society Colour Chart, 2015 Edition, except where general terms of ordinary dictionary significance are used.

Botanical classification: *Phalaenopsis hybrida* 'MI01526'.

Parentage:

*Female parent.*—Proprietary selection of *Phalaenopsis hybrida* identified as code number PHM00322, not patented.

*Male parent.*—Proprietary selection of *Phalaenopsis hybrida* identified as code number PHM00313, not patented.

Propagation:

*Type.*—By in vitro meristem propagation.

*Time to initiate roots, summer.*—About nine to ten weeks at temperatures about 26° C.

*Time to initiate roots, winter.*—About ten to eleven weeks at temperatures about 26° C.

*Time to produce a rooted young plant, summer.*—About 140 to 160 days at temperatures about 26° C.

*Time to produce a rooted young plant, winter.*—About 150 to 180 days at temperatures about 26° C.

*Root description.*—Thick, fleshy; typically grey green in color, towards the apex, close to light green; actual color of the roots is dependent on substrate composition, water quality, fertilizer, substrate temperature and age of roots.

*Rooting habit.*—Small amount of branching; sparse.

Plant description:

*Plant form and growth habit.*—Herbaceous epiphyte; upright plant habit with typically two branched inflorescences per plant, each inflorescence with numerous flowers; monopodial; vigorous growth habit and moderate growth rate.

*Plant height, substrate level to top of foliar plane.*—About 11.5 cm.

*Plant height, substrate level to top of inflorescences.*—About 46 cm.

*Plant diameter or spread.*—About 41 cm.

Leaf description:

*Arrangement and quantity.*—Distichous, simple; sessile; about six leaves per plant.

*Length.*—About 20 cm.

*Width.*—About 8.8 cm.

*Aspect.*—Outwardly arching.

*Shape.*—Elliptic to obovate.

*Apex.*—Acute, slightly unequal.

*Base.*—Sheathing.

*Margin.*—Entire.

*Texture and luster, upper and lower surfaces.*—Furrowed, glabrous; glossy.

*Venation pattern.*—Camptodromous.

*Color.*—Developing leaves, upper surface: Close to NN137A. Developing leaves, lower surface: Close to 137C overlain with close to 59A. Fully expanded leaves, upper surface: Close to 137B; venation, close to 137B. Fully expanded leaves, lower surface: Close to 137C; towards the margins, close to 183B; venation, close to 137C.

Inflorescence description:

*Appearance and flowering habit.*—Showy zygomorphic flowers arranged on axillary branched racemes or panicles; typically two inflorescences per plant; each inflorescence with about 18 open flowers; flowers face outwardly on arching inflorescences supported by upright peduncles; flowers with three petals, two lateral petals and one center petal transformed into a labellum and three sepals.

*Fragrance.*—None detected.

*Time to flower.*—Plants begin flowering about 17 weeks after an inductive cooling period.

*Flower longevity.*—Long flowering period, individual flowers maintain good substance for about 19.5 weeks on the plant; flowers not persistent; plants of the new *Phalaenopsis* resist bud drop during transport.

*Inflorescence length* (*lowermost flower to inflorescence apex*).—About 19.5 cm.

*Inflorescence width.*—About 12 cm by 17 cm.

*Flower buds.*—Height: About 2.7 cm. Diameter: About 1.6 cm. Shape: Ovate. Color: Close to 149B; proximally, tinged with close to 59A.

*Flower diameter.*—About 8.8 cm.

*Flower depth.*—About 5.1 cm.

*Petals, quantity and arrangement.*—Three, two lateral petals and one center petal transformed into a labellum.

*Lateral petals.*—Length: About 4 cm. Width: About 4 cm. Shape: Rhomboid. Apex: Rounded. Margin: Entire. Texture and luster, upper and lower surfaces: Smooth, glabrous, velvety; matte. Color: When opening and fully opened, upper surface: Close to 150D; basal spot, close to 59B; with development, color becoming closer to 155C. When opening and fully opened, lower surface: Close to 150D; basal spot visible from upper surface.

*Labella.*—Appearance: Tri-lobed with two lateral lobes and a central lobe. Length: About 2.9 cm. Width: About 1.4 cm. Shape, lateral lobes: Obovate. Shape, central lobe: Trullate. Apex, lateral lobes: Obtuse. Apex, central lobe: Emarginate with two short and recurved cirrose tips. Margins, lateral and central lobes: Entire. Texture and luster, upper and lower surfaces: Smooth, glabrous, moderately velvety; matte. Callosities: Located at the base of the labellum and attachment point of the lateral petals; about 4 mm in length, about 3 mm in width and about 3 mm in height. Color: When opening and fully opened, upper surface: Lateral lobes: Close to 59B; distally, fading to white to close to 12A. Central lobe: Close to 59B; distally, white and proximally, close to 12A. Callosities: Close to 59B. When opening and fully opened, lower surface: Lateral lobes: Colors visible from upper surface, close to 59B; distally, fading to white to close to 12A. Central lobe: Colors visible from upper surface, close to 59B; distally, white and proximally, close to 12A.

*Sepals.*—Quantity and arrangement: Three, two lower lateral sepals and one upper dorsal sepal. Length, lateral sepal: About 4.3 cm. Width, lateral sepals: About 2.7 cm. Length, dorsal sepal: About 4.7 cm. Width, dorsal sepal: About 3.1 cm. Shape, lateral and dorsal sepals: Elliptic. Apex, lateral sepals: Broadly acute to obtuse. Apex, dorsal sepal: Obtuse to slightly retuse. Base, lateral and dorsal sepals: Rounded. Margin, lateral and dorsal sepals: Entire. Texture and luster, lateral and dorsal sepals, upper and lower surfaces: Smooth, glabrous, velvety; matte. Color, lateral and dorsal sepals: When opening, upper surface: Close to 150D; basal spot, close to 59B; other random spots may occasionally be visible. When opening, lower surface: Close to 150B; basal spot visible from upper surface; other random spots may occasionally be visible. Fully opened, upper surface: Close to 155C; basal spot, close to 59B; other random spots may occasionally be visible. Fully opened, lower surface: Close to 150C; basal spot visible from upper surface; other random spots may occasionally be visible.

*Peduncles.*—Length: About 53 cm. Diameter: About 5 mm. Strength: Strong, somewhat flexible. Aspect: About 10° to 30° from vertical. Texture and luster: Smooth, glabrous; matte. Color: Close to 138A; fine dots, close to 200C.

*Pedicels.*—Length: About 4.2 cm. Diameter: About 4 mm. Strength: Moderately strong. Aspect: About 70° from peduncle axis. Texture and luster: Smooth, glabrous; matte. Color: Close to 150B; proximally, close to 59A.

*Reproductive organs.*—Androecium: Column length: About 1 cm. Column width: About 5 mm. Column color: Close to 155D. Pollinia quantity: Two. Pollinia diameter (per two pollinia): About 3 mm. Pollinia color: Close to 23A. Gynoecium: Stigma length: About 4 mm. Stigma width: About 4 mm. Stigma shape: Reniform. Stigma color: Close to 155A. Ovary length: About 8 mm. Ovary diameter: About 3 mm. Ovary color: Close to 150D.

*Seeds and fruits.*—To date, seed and fruit development have not been observed on plants of the new *Phalaenopsis*.

Pathogen & pest resistance: To date, plants of the new *Phalaenopsis* has been shown to be relatively more tolerant to *Fusarium* spp. than other cultivars of *Phalaenopsis*. To date, plants of the new *Phalaenopsis* have not been shown to be resistant to pests and other pathogens common to *Phalaenopsis* plants.

Temperature tolerance: Plants of the new *Phalaenopsis* have been observed to tolerate high temperatures of about 40° C. and suitable for USDA Hardiness Zone 12.

It is claimed:

1. A new and distinct *Phalaenopsis* plant named 'MI01526' as illustrated and described.

* * * * *